US008865071B2

(12) United States Patent
Lin et al.

(10) Patent No.: US 8,865,071 B2
(45) Date of Patent: Oct. 21, 2014

(54) TEST TAPE DEVICE

(71) Applicant: Roche Diagnostics Operations, Inc., Indianapolis, IN (US)

(72) Inventors: Hao-Chih Lin, Hsinchu (TW); Wen Tsung Wang, Taichung County (TW)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/910,261

(22) Filed: Jun. 5, 2013

(65) Prior Publication Data

US 2013/0267815 A1    Oct. 10, 2013

Related U.S. Application Data

(63) Continuation of application No. PCT/EP2011/072864, filed on Dec. 15, 2011.

(30) Foreign Application Priority Data

Dec. 16, 2010  (EP) ..................... 10195384

(51) Int. Cl.
*G01N 21/00* (2006.01)
*A61B 5/145* (2006.01)
*G01N 35/00* (2006.01)
*G01N 33/487* (2006.01)
*G01N 21/47* (2006.01)

(52) U.S. Cl.
CPC ...... *A61B 5/14532* (2013.01); *G01N 35/00009* (2013.01); *G01N 2201/0415* (2013.01); *G01N 2201/0621* (2013.01); *G01N 2021/478* (2013.01); *G01N 2035/00019* (2013.01); *G01N 33/48764* (2013.01)

USPC ............ 422/66; 422/401; 422/402; 422/408; 422/410; 422/420; 422/547; 422/68.1; 422/82.01; 422/82.02; 422/82.03; 435/287.2; 436/95; 600/365; 600/583; 600/584

(58) Field of Classification Search
USPC ........... 422/401, 402, 408, 410, 420, 547, 66, 422/68.1, 82.01, 82.02, 82.03; 435/287.2; 436/95; 600/365, 583, 584
See application file for complete search history.

(56) References Cited

U.S. PATENT DOCUMENTS

2005/0281706 A1    12/2005    Funke et al.

FOREIGN PATENT DOCUMENTS

| EP | 1362551 A1 | 11/2003 |
| EP | 1500925 A1 | 1/2005 |
| EP | 2138842 A1 | 12/2009 |
| WO | 01/23885 A1 | 4/2001 |
| WO | 2008/111933 A1 | 9/2008 |

*Primary Examiner* — Dennis M White
(74) *Attorney, Agent, or Firm* — Roche Diagnostics Operations, Inc.

(57) ABSTRACT

A test tape device is disclosed herein for use with a replaceable analytical tape cassette, where the device includes a housing having a cassette compartment covered by a cassette door and a housing opening for sample application, a protective cover that can be moved between a closed position covering the housing opening and a release position allowing access to the housing opening and a door lock for retaining the cassette door in the closed position, wherein the protective cover is coupled with the door lock via an interlocking mechanism, such that the door lock can only be unlocked in the release position of the cover.

15 Claims, 2 Drawing Sheets

TEST TAPE DEVICE

CROSS-REFERENCE TO RELATED APPLICATIONS

This patent application is a continuation of Int'l Patent Application No. PCT/EP2011/072864; filed 15 Dec. 2011, which claims the benefit of EP Patent Application No. 10195384.2; filed 16 Dec. 2010. Each patent application is incorporated herein by reference as if set forth in its entirety.

TECHNICAL FIELD

The invention relates generally to engineering and electrochemistry, and more particularly to a test tape device for use of and including a replaceable analytical tape cassette such as those used in blood glucose tests.

BACKGROUND

Many devices are used in practice as blood glucose meters for self-monitoring by diabetics. In one example, a plurality of reactive test fields is provided on a spoolable test tape in a tape cassette. The reactive test fields are examined photometrically after an application of a small amount of a blood sample to determine the glucose content as exactly and reliably as possible. Such tape cassettes are intended to be inserted as a disposable part into a compact, hand-held device housing to allow the necessary analytical steps to be carried out automatically and rapidly. Unfortunately, many such devices may not be reliable, simple or straightforward to produce via a low-cost design especially suitable for mass production. For the foregoing reasons, additional test devices and systems are needed.

BRIEF SUMMARY

On this basis, an object of the present disclosure is to further improve the known test devices and systems and to achieve a reliable, simple and straightforward low-cost design especially suitable for mass production. The disclosure provides a device having safe handling and replacement of a disposable such as a test tape or tape cassette with simple measures. Accordingly, such a device can include a housing having a cassette compartment covered by a cassette door and a housing opening for sample application onto a test tape of the tape cassette. The device also includes a protective cover that can be moved between a closed position covering the housing opening and a release position allowing access to the housing opening, as well as a movable door lock for retaining the cassette door in the closed position. The protective cover can be coupled with the door lock via an interlocking mechanism, such that the door lock is blocked in the closed position of the protective cover and can be unlocked in the release position of the cover.

The tape cassette can be accessed through the housing opening, where the protective cover is provided for protection against damage, dirt or pollution in the unused state. At the same time, replacement of the tape cassette is secured by the interlocking mechanism to avoid possible damage by interfering structural parts. In the closed position of the protective cover, the interlocking mechanism engages the door lock and blocks it unmovable. Only in the release position of the cover does the interlocking mechanism disengage from the door lock, such that the door lock is movable and can be unlocked. Thereby, the cassette door can be opened only in the release position of the cover, such that the user can easily insert and remove the tape cassette. Specifically, in the release position of the cover and the open position of the cassette door, the housing opening and the cassette compartment opening form a combined aperture for simplified exchange of the tape cassette. Advantageously, it should be noted that such devices may be handled by users or diabetics themselves even under critical physical conditions.

In one embodiment, the interlocking mechanism can have a swivel-mounted lock catch that can be turned by a movement of the protective cover about a swivel axis. This allows a mechanically simple and reliable latching in connection with the operation of the protective cover. In this connection, it is advantageous when the lock catch has two arms—an actuator arm that engages into a movement path of the protective cover, and a blocking arm that blocks the door lock in a blocking position.

In another embodiment, the interlocking mechanism can be configured to block the door lock automatically in the closed position of the protective cover. This can be manufactured particularly advantageously when the interlocking mechanism is biased by a return spring against a stop.

A further manufacturing and functional simplification can be achieved when the door lock has a slider for manual operation, and the slider is provided with a hook member that can be hooked to the cassette door in the closed state.

To further ease the operation, it is advantageous when the cassette door is moved to an open position upon actuation of the unlocked door lock by means of a biased door spring preferably arranged on a door hinge.

For shielding a protruding tip of the tape cassette, it is particularly advantageous when the protective cover has a sliding member that is moveably supported in a preferably arc-shaped sliding track of the housing.

To provide a simple structure for detecting whether the opening is covered or not, the sliding member may carry a contact element that directly actuates a position indicator switch in each of the closed and release position of the protective cover.

A refinement can be achieved when the sliding member carries a pusher element that unlocks the interlocking mechanism when moving the protective cover to the release position. In one embodiment, a cross-member that protrudes at the side of the sliding member forms at the same time the contact element and actuating element.

Another refinement in handling is because the protective cover is detachably secured in the closed and release position by means of a stop connection. Advantageously, the stop connection comprises a leaf spring that is mounted in a housing wall that borders the sliding track and that engages with its spring ends to a catch element of the sliding member.

In another embodiment, the tape cassette has a cassette tip for application of a body fluid, and the cassette door forms a boundary of the housing opening. Preferably, the shell-type protective cover in the closed position encloses the cassette tip on all sides. The tape cassette can be exchanged from the cassette compartment without collision when the protective cover is in the release position and the cassette door is open. In this state, a combined housing aperture is formed by the housing opening and the cassette compartment opening.

These and other advantages, effects, features and objects of the invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
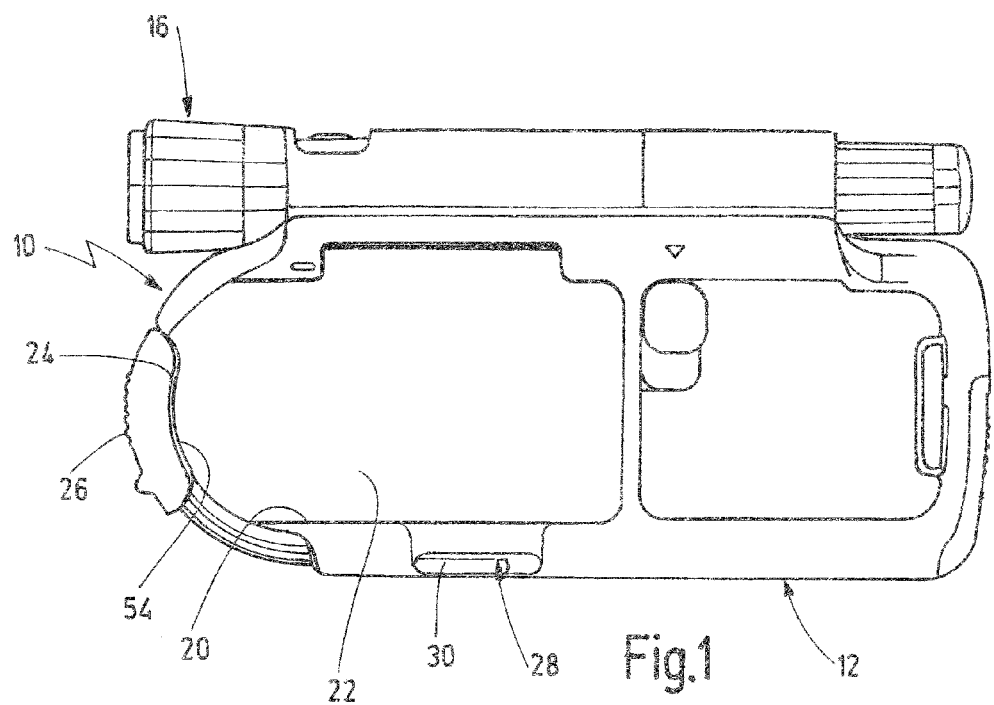
FIG. 1 is a rear side view of an embodiment of a tape cassette-type glucose meter with an attached lancing aid in the closed position of both a cassette compartment and a protective cover.

While the present invention is susceptible to various modifications and alternative forms, exemplary embodiments thereof are shown by way of example in the drawings and are herein described in detail. It should be understood, however, that the description of exemplary embodiments that follows is not intended to limit the invention to the particular forms disclosed, but on the contrary, the intention is to cover all advantages, effects, features and objects falling within the spirit and scope of the invention as defined by the embodiments above and the claims below. Reference should therefore be made to the embodiments above and claims below for interpreting the scope of the invention. As such, it should be noted that the embodiments described herein may have advantages, effects, features and objects useful in solving other problems.

DESCRIPTION OF PREFERRED EMBODIMENTS

The test tape devices and systems now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the test tape devices and systems described herein will come to mind to one of skill in the art having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Test Tape Devices and Systems

The drawings show a test tape device configured as a portable glucose meter 10 for self-monitoring of blood glucose and comprising a housing 12 for inserting a disposable analytical tape cassette 14. A lancing aid 16 is attached to the housing 12 to lance the skin by users such as diabetics and to collect a blood sample that then can be applied to a test tape 18 contained in the tape cassette 14.

FIG. 1 shows the glucose meter 10 from the rear side with a cassette compartment 20 covered by a cassette door 22 and a housing opening 24 for sample application closed by a protective cover 26. A door lock 28 configured for retaining the cassette door 22 in a closed position is manually releasable by a door button 30. The protective cover 26 can be moved between the closed position and a release position allowing access to the housing opening 24.

Figure 2:
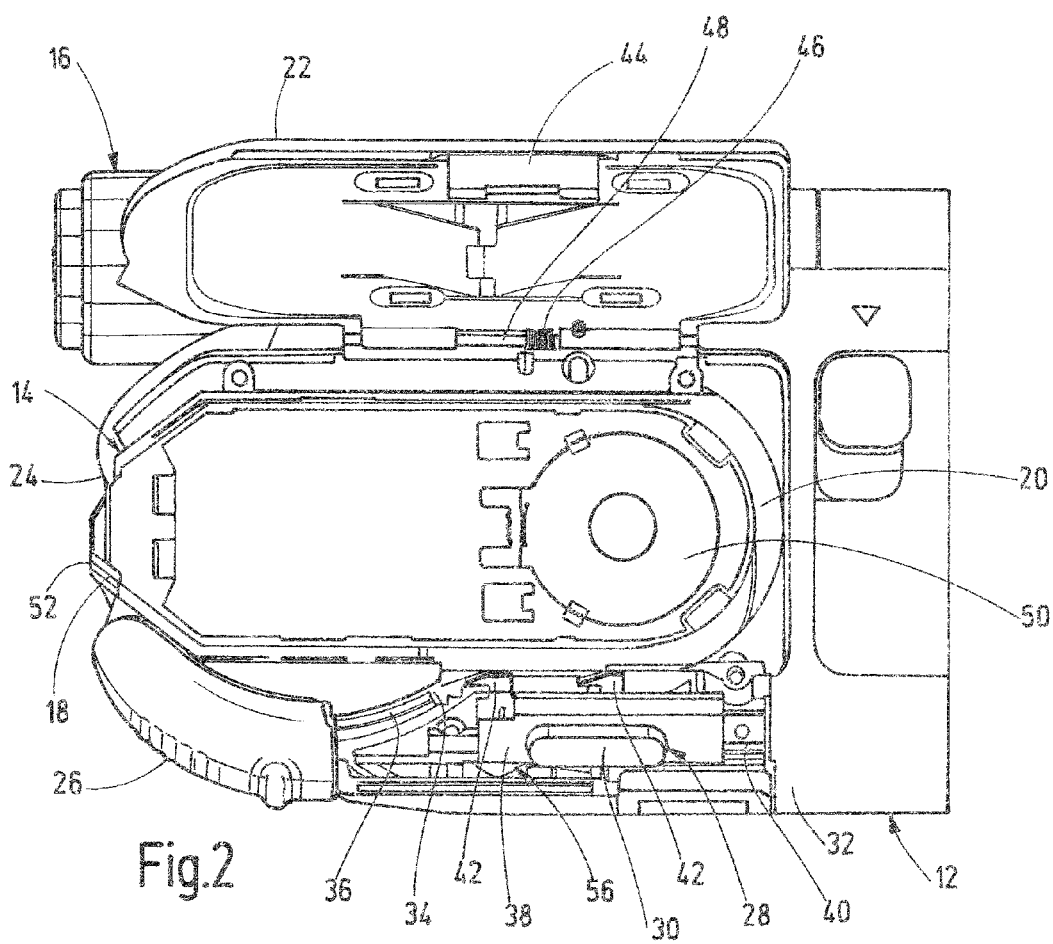
FIG. 2 is a partly expanded perspective view of the glucose meter of FIG. 1 with an open cassette door and an open protective cover.

FIG. 2 illustrates the inside structure of the device 10 with open cassette door 22 and protective cover 26 moved to the release position. A sidewall 32 of the housing 12 is shown partially cutaway to reveal an arc-shaped sliding track 34 in which a sliding member 36 connected to the cover 26 is moveably supported. In the open state, the uncovered opening of the cassette compartment 20 and the housing opening 24 form a combined aperture for unhindered exchange of the tape cassette.

As FIG. 2 further elucidates, the door lock 28 has a slider 38 connected to the door button 30 and being slidable in a linear guidance 40 between an unlocked and a locked state. The slider 38 is provided with hook members 42 that can be hooked to a fishing plate 44 on the inside of the cassette door 22. In the unlocked state of the slider 38, the cassette door 22 is urged to an open position by means of a biased door spring 46 arranged at the door hinge 48.

The tape cassette 14 comprises two spools 50 to transport sections of the test tape 18 over a cassette tip 52, such that body fluid (e.g., blood) can be applied to reactive test fields on the tape. The cassette tip 52 protrudes through the housing opening 24 to facilitate sample application. In the closed position, the cassette door 22 forms a boundary 54 of the housing opening 24, and the shell-type protective cover 26 encloses the cassette tip 52 on all sides (see, FIG. 1). Therefore, the tape cassette 14 can be exchanged from the cassette compartment 20 only when the cassette door 22 is open and the protective cover 26 is in the release position at the same time, as clearly noticeable in FIG. 2.

Figure 3:
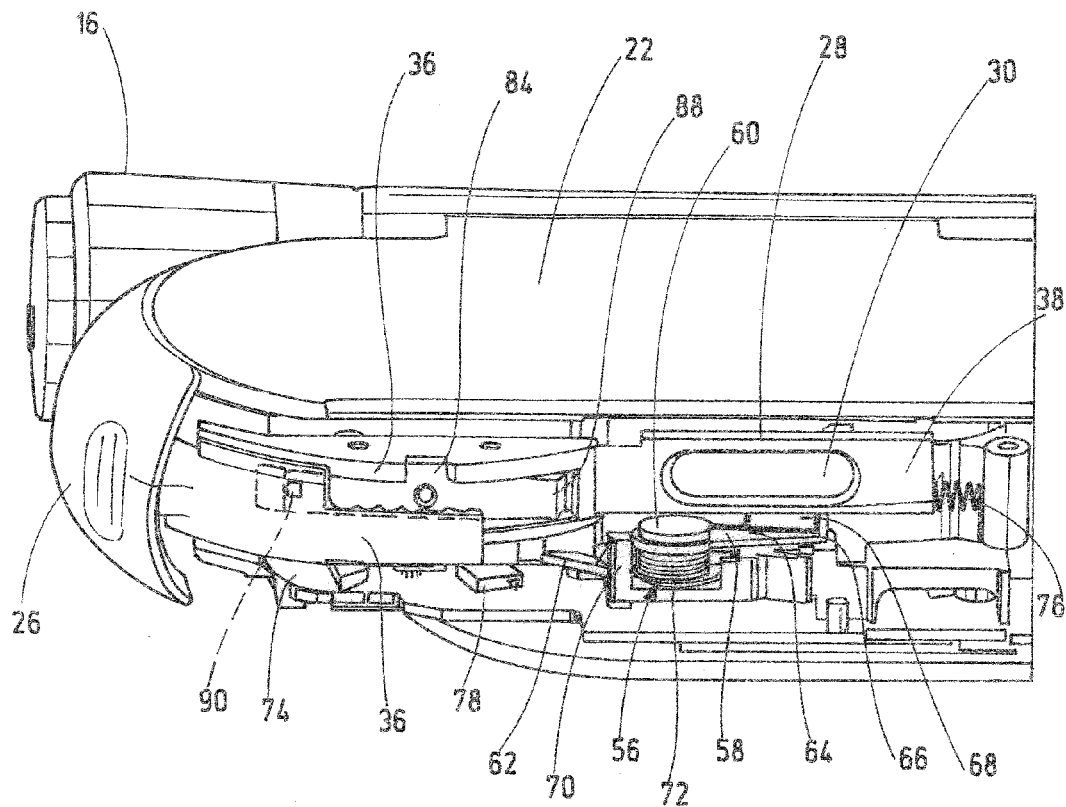
FIG. 3 is a partly expanded and cutaway side view of the glucose meter of FIG. 1.
Figure 4:
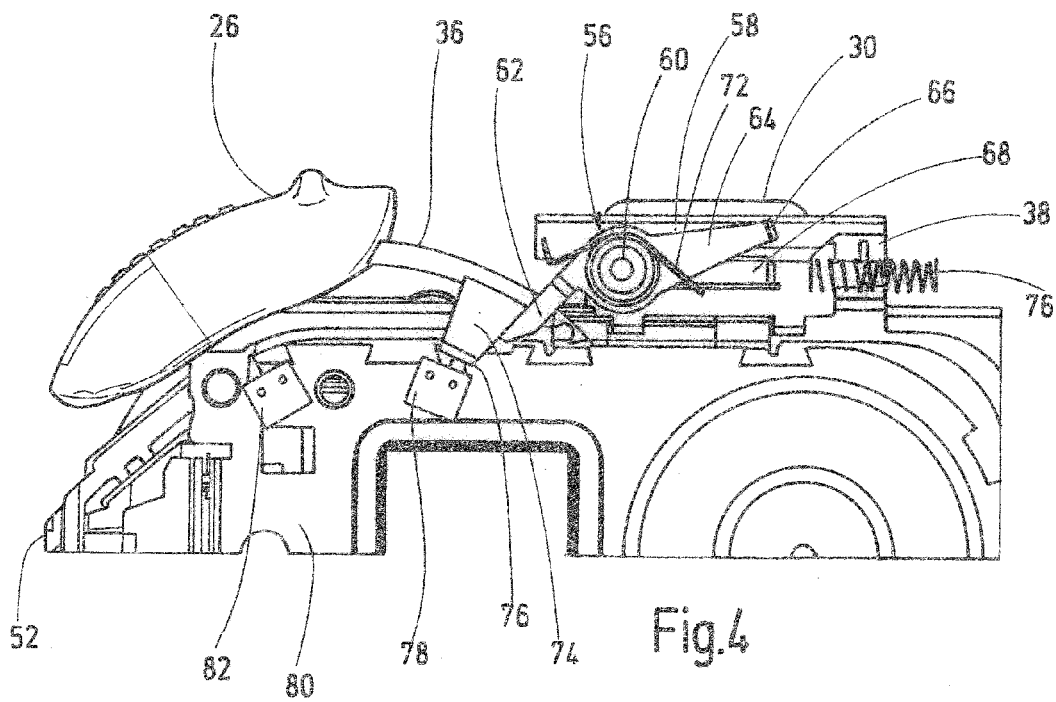
FIG. 4 is a partly cutaway top view of the glucose meter of FIG. 1.

To allow users to insert the tape cassette 14 into the meter 10 and to take it out from the meter 10 conveniently without collision, the protective cover 26 is coupled with the door lock 28 by means of an interlocking mechanism 56, as illustrated in FIGS. 3 and 4. Consequently, the door lock 28 is blocked in the closed position of the protective cover 26 and can be unlocked only in the release position of the cover 26.

For this purpose, the interlocking mechanism 56 has a swivel-mounted lock catch 58 that is supported on a swivel axis 60 and that can be activated by a movement of the protective cover 26 into the release position. The lock catch 58 includes an actuator arm 62 engaging into the movement path of the sliding member 36 and a blocking arm 64 that blocks the door lock 28 in a blocking position. For this purpose, the blocking arm 64 has a hooking part 66 at its end operable to engage behind a protrusion 68 of the slider 28.

As illustrated in FIG. 3, when the protective cover 26 is in the closed position, the actuator arm 62 is urged against a stop 70 by means of a helical return spring 72 wound around the swivel axis 60, and thus the door lock 28 is blocked automatically due to a form closure of the hooking part 66 and the protrusion 68.

As can be seen best from FIG. 4, the sliding member 36 of the protective cover 26 carries an attachment 74 on its side. When the sliding member 36 slides on the sliding track 34 until the attachment 74 pushes the actuator arm 62, it makes the lock catch 58 rotate to a position out of engagement with the slider 38, such that the door button 30 can be moved against the spring 76 to open the door 22.

The free end of the attachment 74 provides an additional function as a contact element 76 for detecting the end positions of the protective cover 26. Specifically, the contact element 76 directly contacts the switch 78 on a circuit board 80 of the meter 10 when the cover 26 is in the release position. Similarly, the contact element 76 directly operates the switch 82 when the cover 26 slides back on the track 34 and covers the housing opening 24.

To avoid a loose state of the cover 26, a stop connection is operative in the closed and release position. As shown in FIG. 3, the stop connection is provided as a leaf spring 84 mounted in a recess of the housing wall 86 bordering the sliding track 34. The leaf spring 84 has curved ends 88 that engage to a catch element 90 protruding on the rear side of the sliding member 36 and depicted in phantom lines in FIG. 3. In this manner, the user receives a haptic feedback when the cover 26 assumes its end positions.

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

The invention claimed is:

1. A test tape device including a replaceable analytical tape cassette, the device comprising:
   a housing having a cassette compartment covered by a cassette door and a housing opening for sample application onto a test tape of the analytical tape cassette;
   a protective cover that can be moved between a closed position covering the housing opening and a release position allowing access to the housing opening;
   a door lock for retaining the cassette door in the closed position, wherein the protective cover is coupled with the door lock via an interlocking mechanism, and wherein the door lock is blocked in the closed position of the protective cover and can be unlocked in the release position of the protective cover; and
   a biased door spring coupled to the cassette door, wherein the cassette door is moved to an open position by means of the biased door spring.

2. The test tape device of claim 1, wherein the interlocking mechanism has a swivel-mounted lock catch that can be turned by a movement of the protective cover about a swivel axis.

3. The test tape device of claim 2, wherein the lock catch has two arms, such that a first arm is an actuator arm that engages into a movement path of the protective cover and a second arm is a blocking arm that blocks the door lock in a blocking position.

4. The test tape device of claim 1, wherein the interlocking mechanism is configured to block the door lock automatically in the closed position of the protective cover.

5. The test tape device of claim 1, wherein the interlocking mechanism is biased by a return spring against a stop.

6. The test tape device of claim 1, wherein the door lock has a slider for manual operation, and wherein the slider is provided with a hook member that can be hooked to the cassette door in the closed state.

7. The test tape device of claim 1, wherein the door spring is arranged on a door hinge.

8. The test tape device of claim 1, wherein the protective cover has a sliding member that is moveably supported in a sliding track of the housing.

9. The test tape device of claim 8, wherein the sliding member carries a pusher element that unlocks the interlocking mechanism when moving the protective cover to the release position.

10. The test tape device of claim 8, wherein the sliding member carries a contact element that directly actuates a position indicator switch in each of the closed and release position of the protective cover.

11. The test tape device of claim 10, wherein a cross-member that protrudes at the side of the sliding member forms at the same time pusher element and the contact element.

12. The test tape device of claim 1, wherein the protective cover is detachably secured in the closed and release position by means of a stop connection.

13. The test tape device of claim 12, wherein the stop connection comprises a leaf spring mounted in a housing wall bordering the sliding track and engages with its spring ends to a catch element of the sliding member.

14. The test tape device of claim 1, wherein the tape cassette has a cassette tip for application of a body fluid, wherein the cassette door forms a boundary of the housing opening, and wherein the protective cover in the closed position encloses the cassette tip on all sides.

15. The test tape device of claim 1, wherein the tape cassette can be exchanged from the cassette compartment without collision when the protective cover is in the release position and the cassette door is open.

* * * * *